(12) United States Patent
O'Grady et al.

(10) Patent No.: US 9,019,345 B2
(45) Date of Patent: Apr. 28, 2015

(54) IMAGING MODE BLOOMING SUPPRESSION

(75) Inventors: Patrick O'Grady, Alameda, CA (US);
Ian McDowall, Woodside, CA (US);
Brian D. Hoffman, Mountain View, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 843 days.

(21) Appl. No.: 12/855,957

(22) Filed: Aug. 13, 2010

(65) Prior Publication Data

US 2012/0002012 A1    Jan. 5, 2012

Related U.S. Application Data

(60) Provisional application No. 61/361,233, filed on Jul. 2, 2010.

(51) Int. Cl.
| | | |
|---|---|---|
| H04N 13/00 | (2006.01) | |
| H04N 13/02 | (2006.01) | |
| A61B 6/02 | (2006.01) | |
| H04N 13/04 | (2006.01) | |

(52) U.S. Cl.
CPC ............ *H04N 13/0239* (2013.01); *A61B 6/022* (2013.01); *H04N 13/0402* (2013.01); *H04N 13/0497* (2013.01)

(58) Field of Classification Search
None
See application file for complete search history.

(56) References Cited

U.S. PATENT DOCUMENTS

| | | | |
|---|---|---|---|
| 6,331,181 B1 | 12/2001 | Tierney et al. | |
| 6,537,211 B1 * | 3/2003 | Wang et al. | 600/178 |
| 6,711,481 B1 * | 3/2004 | King et al. | 701/36 |
| 6,720,988 B1 | 4/2004 | Gere et al. | |
| 2002/0062061 A1 * | 5/2002 | Kaneko et al. | 600/118 |
| 2002/0093563 A1 * | 7/2002 | Cline et al. | 348/65 |
| 2002/0177751 A1 * | 11/2002 | Ueno et al. | 600/160 |
| 2004/0095554 A1 * | 5/2004 | Ono | 351/206 |
| 2004/0109231 A1 * | 6/2004 | Haisch et al. | 359/385 |
| 2006/0092273 A1 | 5/2006 | Gere et al. | |
| 2007/0046827 A1 * | 3/2007 | Harada | 348/672 |
| 2008/0024679 A1 * | 1/2008 | Lee | 348/731 |
| 2008/0065105 A1 | 3/2008 | Larkin et al. | |
| 2008/0198246 A1 * | 8/2008 | Gardner | 348/254 |
| 2008/0239070 A1 * | 10/2008 | Westwick et al. | 348/68 |
| 2009/0021578 A1 * | 1/2009 | Yamazaki et al. | 348/65 |

(Continued)

FOREIGN PATENT DOCUMENTS

WO    WO2010/042522 A1    4/2010

OTHER PUBLICATIONS

U.S. Appl. No. 12/575,093, filed Oct. 7, 2009.

(Continued)

*Primary Examiner* — Christopher S Kelley
*Assistant Examiner* — Kaitlin A Retallick

(57) ABSTRACT

A minimally invasive surgical system includes a scene anti-bloom process that allows switching between imaging modes on a stereoscopic display without causing a surgeon to look-away or being momentarily distracted by sudden changes in overall scene luminance. The process receives a switch from a first imaging mode to a second imaging mode. An overall scene luminance of a scene in the first imaging mode is less than an overall scene luminance of a scene in the second imaging mode. The process delays the switch to the second imaging mode until after an illumination output level of a visible illumination source has changed to a higher output level, and then switches to the second imaging mode.

16 Claims, 4 Drawing Sheets

(56) References Cited

U.S. PATENT DOCUMENTS

| | | | |
|---|---|---|---|
| 2009/0270678 A1* | 10/2009 | Scott et al. | 600/109 |
| 2010/0066858 A1* | 3/2010 | Asoma | 348/229.1 |
| 2011/0193967 A1* | 8/2011 | Matsumoto et al. | 348/164 |
| 2012/0004508 A1* | 1/2012 | McDowall et al. | 600/178 |
| 2012/0004557 A1* | 1/2012 | McDowall et al. | 600/476 |

OTHER PUBLICATIONS

Vertut, Jean and Phillipe Coiffet, *Robot Technology: Teleoperation and Robotics Evolution and Development*, English translation, Prentice-Hall, Inc., Inglewood Cliffs, NJ, USA 1986, vol. 3A, 332 pages.

* cited by examiner

IMAGING MODE BLOOMING SUPPRESSION

RELATED APPLICATION

This application claims priority to and the benefit of: U.S. Provisional Application No. 61/361,233 filed Jul. 2, 2010 entitled "IMAGING MODE BLOOMING SUPPRESSION," naming as inventors, Patrick O'Grady, Ian McDowall, and Brian D. Hoffman, which is incorporated herein by reference in its entirety.

BACKGROUND

1. Field of Invention

Aspects of this invention are related to endoscopic imaging and are more particularly related to switching between imaging modes having different overall scene luminance.

2. Related Art

The da Vinci® Surgical System, commercialized by Intuitive Surgical, Inc., Sunnyvale, Calif., is a minimally invasive teleoperated surgical system that offers patients many benefits, such as reduced trauma to the body, faster recovery and shorter hospital stay. One key component of the da Vinci® Surgical System is a capability to provide two-channel (i.e., left and right) video capture and display of the captured visible images to provide stereoscopic viewing for the surgeon.

Such electronic stereoscopic imaging systems may output high definition video images to the surgeon, and may allow features such as zoom to provide a "magnified" view that allows the surgeon to identify specific tissue types and characteristics, as well as to work with increased precision. In a typical surgical field, however, certain tissue types are difficult to identify, or tissue of interest may be at least partially obscured by other tissue. This complicates the surgical procedure.

SUMMARY

In one aspect, a minimally invasive surgical system includes a scene anti-bloom process that allows switching between imaging modes on a stereoscopic display without causing a surgeon either to look-away from, or be distracted by, sudden changes in overall scene luminance. In one aspect, the process receives a command to switch from a first imaging mode to a second image mode of the display. An overall scene luminance of a scene in the first imaging mode is less than an overall scene luminance of a scene in the second imaging mode. The process delays the switch to the second imaging mode until after an illumination output level of a visible illumination source has changed to a higher output level, and then switches to the second imaging mode.

In one aspect, the first and second imaging modes have a same normal level of a display output gain of a display of the minimally invasive surgical system. In this aspect, the delaying includes lowering the display output gain of the display from the normal level. The delaying also includes switching from a lower illumination output level of the visible illumination source to a higher illumination output level of the visible illumination source following lowering the display output gain. In another aspect, the switching the imaging mode includes restoring the display output gain to the normal level.

A minimally invasive surgical system includes a display, an output gain control unit coupled to the display, an imaging mode switch, and a controller coupled to the output gain control unit and to the imaging mode switch. Following receipt of an imaging mode change command from the image mode switch, the controller configures the output gain control unit to attenuate an output image by decreasing the brightness of the output image.

In one aspect, the system also includes an illuminator including a power and level controller and a visible light source. The controller configures the power and level controller to restore an output level of the visible light source from a reduced output level to a normal illumination output level. In another aspect, the reduced output level corresponds to the visible light source being powered off. In yet another aspect, the reduced output level is less than one hundred percent of the normal illumination output level. Following the restoration of the output level of the visible light source the controller configures the output gain control unit to display an image on the display.

Figure 1:
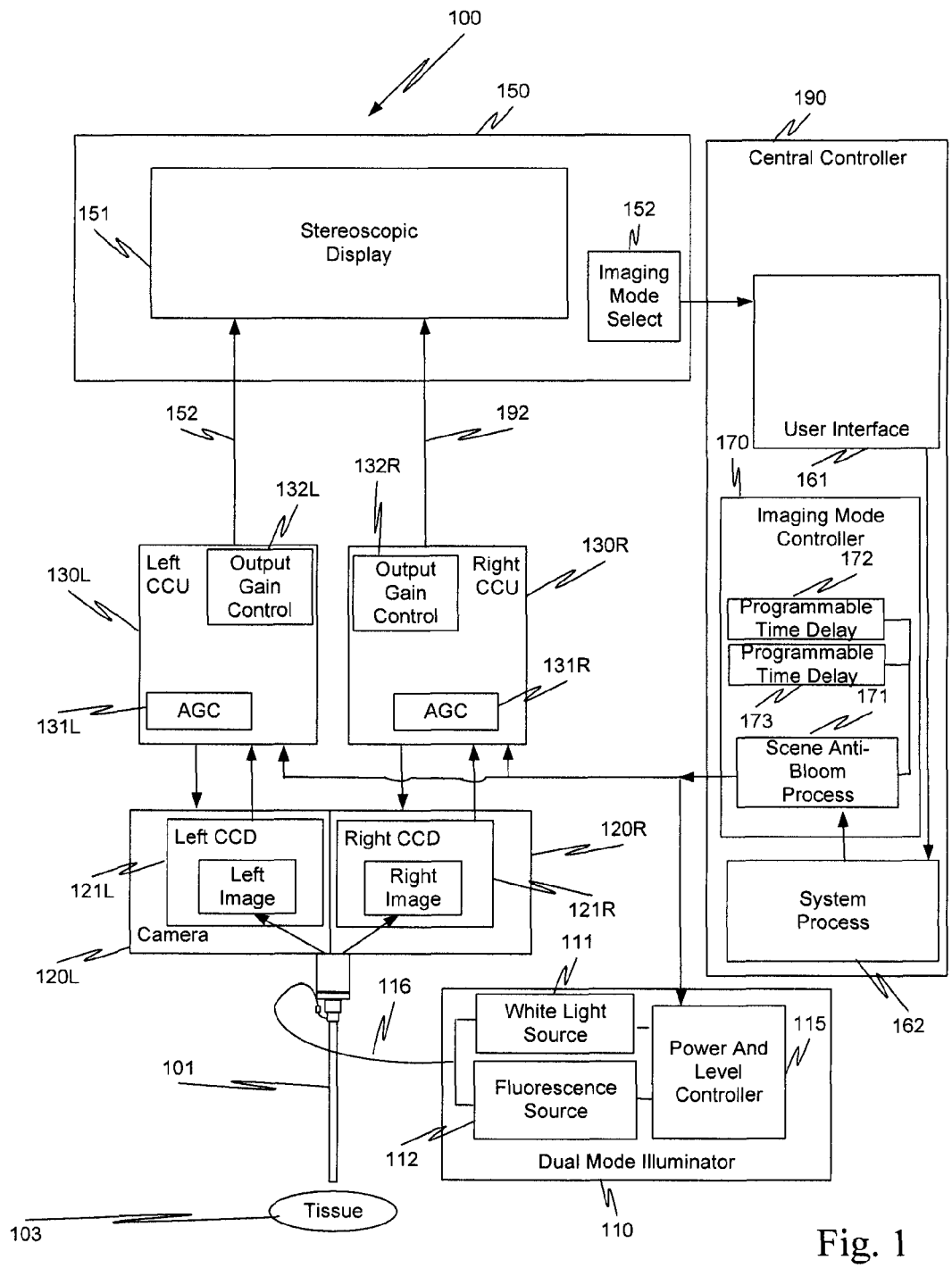
FIG. 1 is a high level diagrammatic view of a minimally invasive teleoperated surgical system that includes an imaging mode controller having a scene anti-bloom process.

In the drawings, the first digit of a reference number indicates the figure in which the element with that reference number first appeared.

DETAILED DESCRIPTION

In one aspect, minimally invasive surgical system 100 (FIG. 1) includes a scene anti-bloom process 171 that facilitates switching between imaging modes on stereoscopic display 151 without causing a surgeon to look away from or to be distracted by sudden changes in overall scene luminance. In some conventional minimally invasive surgical systems, when the surgeon switches the imaging mode of stereoscopic display 151 from a fluorescence imaging mode to a normal imaging mode, e.g., switches from illuminating tissue 103 with illumination from fluorescence illumination source 112 to illuminating tissue 103 with the normal output illumination of white light illumination source 111, the display of the scene that includes tissue 103 becomes extremely bright and washed out, i.e., the displayed scene blooms.

In these conventional minimally invasive surgical systems, the displayed scene is so bright that typically the surgeon may divert his or her eyes from display 151. As explained more completely below, aspects of this invention eliminate this blooming and so enhance the surgeon's performance, because the surgeon can continue viewing display 151 during all imaging mode changes.

FIG. 1 is high level diagrammatic views of a minimally invasive teleoperated surgical system 100, for example, the da Vinci® Surgical System commercialized by Intuitive Surgical System, Inc. of Sunnyvale Calif. Surgical system 100 includes an imaging mode controller 170 with scene anti-bloom process 171. As explained more completely below, when the surgeon switches the imaging mode from scenes of tissue 103 with a low overall scene luminance (a first overall scene luminance) to scenes with a high overall scene luminance (a second, higher overall scene luminance), scene anti-bloom process 171 attenuates the brightness of any scenes displayed on display 151 until after the illumination has been changed and until after any causes of blooming associated with the change in illumination have stabilized. Thus, scene anti-bloom process 171 eliminates the very bright scenes that are encountered in the conventional minimally invasive surgical systems when the imaging mode is changed.

Prior to considering process 171 in further detail, it is informative to understand the operation of system 100 as illustrated in FIG. 1. There are other parts, cables etc. associated with the da Vinci® Surgical System, but these are not illustrated in FIG. 1 to avoid detracting from the disclosure. Further information regarding minimally invasive surgical systems may be found for example in U.S. patent application Ser. No. 11/762,165 (filed Jun. 13, 2007; disclosing Minimally Invasive Surgical System) and U.S. Pat. No. 6,331,181 (filed Dec. 18, 2001; disclosing Surgical Robotic Tools, Data Architecture, and Use), both of which are incorporated herein by reference.

For example, while it is not shown in FIG. 1, system 100 includes a cart with a plurality of servo controlled robotic manipulators. Each manipulator can be coupled to, and decoupled from master tool manipulators on surgeon's console 150. A stereoscopic endoscope 101 is mounted on one of the manipulators. The interactions between the master tool manipulators, the slave surgical devices, and stereoscopic endoscope 101 are the same as in a conventional system and so are known to those knowledgeable in the field.

Also, as explained more completely below, acquired images of a surgical site are directed to stereoscopic display 151. However, each acquired image (left or right) can be directed to more places than just this display. For example, other monitors, video recorders, video codecs for remote display via the Internet can all be used with system 100. The following description is directed at eliminating blooming so that the surgeon keeps his or her eyes on display 151. However, the processes described herein are also applicable to any of the contexts of these other devices. Therefore, eliminating blooming on display 151 is illustrative only and is not intended to be limiting.

Also, in the following example, a stereoscopic endoscope, left and right acquisition and display paths are described. This also is illustrative only. The processes described more completely below also are applicable to monoscopic systems that switch between normal and fluorescence imaging mode, as described herein.

As described more completely below, endoscope 101 provides left and right images of tissue 103 within a patient. The left and right images also include images of any slave surgical devices in the field of view of stereoscopic endoscope 101. The collection of images in a frame acquired from a channel of endoscope 101 is referred to herein as a scene. The acquired scene has an overall luminance. Overall luminance is used to distinguish the scene luminance from the luminance of individual images in the acquired scene, i.e., the luminance is over all of the images in the acquired scene.

In system 100, an illumination system, e.g., dual mode illuminator 110, is coupled to endoscope 101. Dual mode illuminator 110 includes a white light source 111 and a fluorescence excitation source 112. The on and off state of each of sources 111 and 112 is independently controllable by power and level controller 115 in response to commands from imaging mode controller 170. In addition, at least the output level of white light source 111 is controlled by power and level controller 115 in response to commands from imaging mode controller 170.

Typically, three (or more) visible color components make up white light, i.e., white light includes a first visible color component, a second visible color component, and a third visible color component. Each of the three visible color components is a different visible color component, e.g., a red component, a green component, and a blue component.

In one aspect, white light source 111 includes a source for each of the different visible color illumination components. For a red-green-blue implementation, in one example, the sources are lasers.

The use of lasers in white light source 111 is illustrative only and is not intended to be limiting. White light source ill could also be implemented with multiple laser diodes or light emitting diodes (LEDs) for example. Alternatively, white light source 111 could use a Xenon lamp with an elliptic back reflector and a long band pass coating to create broadband white illumination light for visible images. The use of a Xenon lamp also is illustrative only and is not intended to be limiting. For example, a high pressure mercury arc lamp, other arc lamps, or other broadband light sources may be used.

When the fluorescence excitation wavelength occurs outside the visible spectrum (e.g., in the near infrared (NIR) spectrum), a laser module (or other energy source, such as a light-emitting diode or filtered white light) is used as fluorescence excitation source 112.

In one example, dual mode illuminator 110 has a normal imaging mode and a fluorescence imaging mode. In the normal imaging mode, white light source 111 provides illumination that illuminates tissue 103 in white light. The illumination output of white light source 111 in the normal imaging mode is referred to as the normal illumination output level of white light source 111. Fluorescence excitation source 112 is not used in the normal imaging mode.

In the fluorescence imaging mode, fluorescence excitation source 112 is turned on. Fluorescence excitation source 112 provides a fluorescence excitation illumination component that excites fluorescence from tissue. For example, narrow band light from fluorescence excitation source 112 is used to excite tissue-specific fluorophores so that fluorescence images of specific tissue within the scene are acquired by cameras 120L, 120R.

In the fluorescence imaging mode, white light source 111 provides, in one aspect, one or more visible color illumination components to illuminate tissue 103. If one or more visible color illumination components are used in the fluorescence imaging mode, the output level of those visible color illumination components is reduced to one part in ten relative to the normal illumination output level used in the normal imaging mode. In this aspect, both visible and fluorescence images are acquired. In another aspect, none of the visible color components of white light are used when fluorescence excitation source 112 is on.

In any of the modes of operation of dual mode illuminator 110, the light from the light source or light sources is directed into a fiber optic bundle 116. Fiber optic bundle 116 provides the light to an illumination path in stereoscopic endoscope 101 that in turn directs the light to tissue 103.

Endoscope 101 also includes, in this aspect, two optical channels for passing light emanating from tissue 103 and from any other objects in the field of view of endoscope 101. Reflected white light or a reflected visible color component of white light forms a visible image or images. Fluorescence may be either visible light or non-visible light depending on the fluorophore that is used. In the fluorescence imaging mode, an overall scene luminance of an acquired frame is generally much less than the overall scene luminance of an acquired frame in the normal imaging mode.

The light from tissue 103 (FIG. 1) is passed by the stereoscopic optical path in endoscope 101 to cameras 120L, 120R.

In the various modes of operation that correspond to the various imaging modes, left image CCD 121L acquires a frame that includes a left image and right image CCD 121R acquires a frame that includes a right image. Each of left image CCD 121L and right image CCD 121R can be multiple CCDs that each capture a different visible color component; a single CCD with different regions of the CCD that capture a particular visible color component, etc. A three-chip CCD sensor is illustrative only. A single CMOS image sensor with a color filter array or a three-CMOS color image sensor assembly may also be used.

Camera 120L is coupled to a stereoscopic display 151 in surgeon's console 150 by a left camera control unit 130L. Camera 120R is coupled to stereoscopic display 151 in surgeon's console 150 by a right camera control unit 130R. Camera control units 130L, 130R receive signals from an imaging mode controller 170 and provide control signals to cameras 120L, 120R. Each of camera control units 130L, 130R includes an automatic gain controller (AGC) 131L, 131R.

In one aspect, each of camera control units 130L, 130R also includes an output gain control unit 132L, 132R that controls the display output gain for display 151. The inclusion of output gain control units 132L, 132R in camera control units 130L, 130R is illustrative only and is not intended to be limiting. In another aspect, output gain control units 132L, 132R are units positioned between camera control units 130L, 130R and display 151. In still another aspect, output gain control units 132L, 132R are included in display 151.

Automatic gain controllers 131L, 131R automatically adjust the gain for the acquired frames from cameras 120L and 120R. The output display gain can be set by commands from imaging mode controller 170 to output gain control units 132L, 132R.

When the illumination from dual mode illuminator 110 changes, the overall scene luminance of the acquired frames change. In changing from illumination in the fluorescence imaging mode to illumination in the normal imaging mode, the automatic gain controllers 131L, 131R are configured for the relatively lower overall scene luminance of frames acquired in the fluorescence imaging mode. However, upon the illumination source switch, the acquired frames have the normal overall scene luminance, which is greater than the overall scene luminance for the frames in the fluorescence imaging mode. Consequently, immediately following the switch, the automatic gain controller is not configured correctly, and in the conventional systems this contributed to the scene blooming.

In one aspect, stereoscopic video output display 151, sometimes referred to as display 151, may be operated in various imaging modes. For example, in a normal imaging mode, only visible images are output to display 151. In fluorescence imaging mode, fluorescence images are superimposed on visible images to create augmented images, and the augmented images are output to display 151. One technique for superimposing the images is described below.

Figure 2:
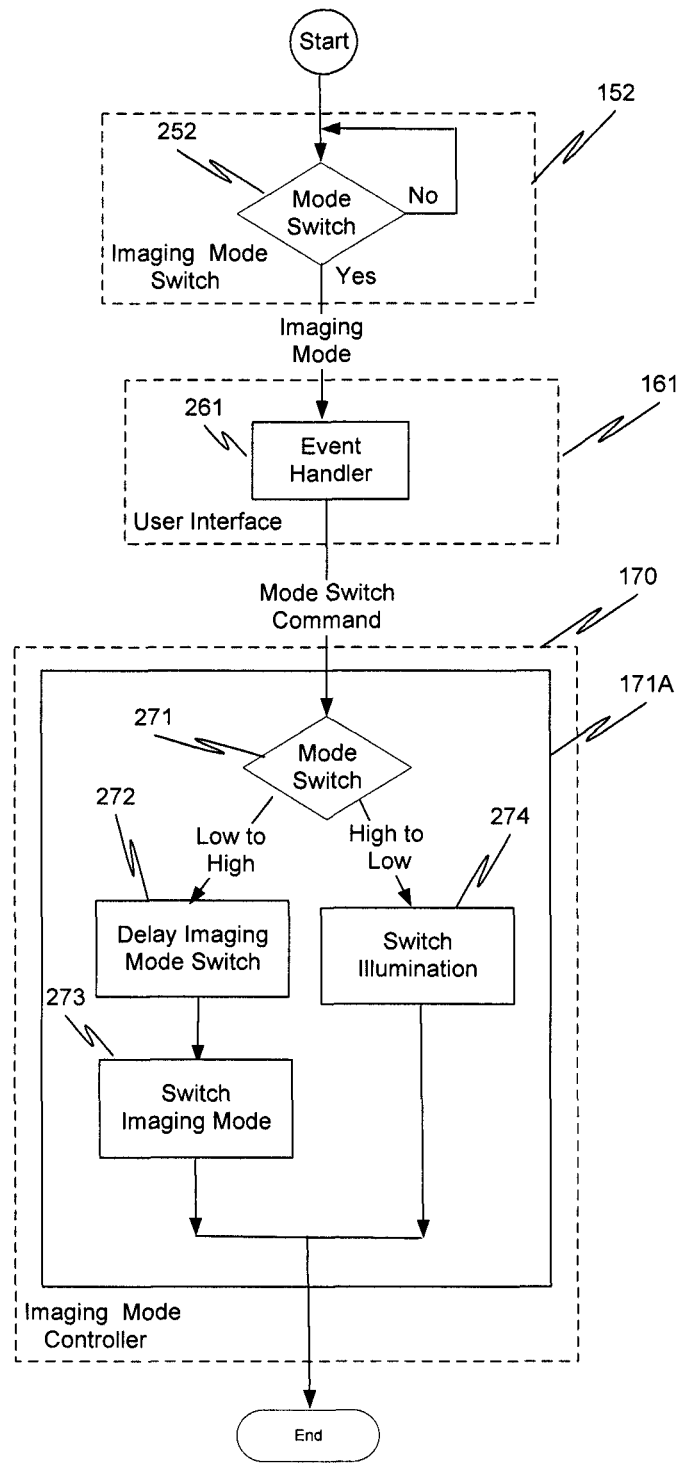
FIG. 2 is a process flow diagram for one aspect of the scene anti-bloom process.

The imaging mode of display 151, in one aspect, is toggled between these two imaging modes by using imaging mode select switch 152, e.g., a foot switch, a double click of the master grips that control the surgical instruments, voice control, and other like switching methods. In response to the user input, a MODE SWITCH check operation 252 (FIG. 2) in imaging mode select switch 152 sends a notification of the selected imaging mode to an EVENT HANDLER 261 in a user interface 161. FIG. 2 is a process flow diagram of one aspect of a method to suppress blooming.

In response to the notification, EVENT HANDER 261 in user interface 161 sends a mode switch command to system process 162. System process 162 forwards the mode switch command to imaging mode controller 170 and also configures any other elements of system 100 needed to process the acquired images so that the surgeon is presented the requested imaging mode in display 151. System process 162 represents the various controllers, etc. in system 100 that are not illustrated in FIG. 1.

MODE SWITCH check operation 271, in imaging mode controller 170, determines the direction of the change in overall scene luminance. If the imaging mode is changed from the normal imaging mode to the fluorescence imaging mode, the direction of the change in overall scene luminance is high to low. Conversely, if the imaging mode is changed from the fluorescence imaging mode to the normal imaging mode, the direction of the change in overall scene luminance is low to high. As explained above, in the fluorescence imaging mode, the illumination output from white light source 111 in illuminator 110 is less than the illumination output from white light source 111 from illuminator 110 in the normal imaging mode.

When the imaging mode switch is low to high, MODE SWITCH check operation 271 transfers to DELAY IMAGING MODE SWITCH process 272. In DELAY IMAGING MODE SWITCH process 272, imaging mode controller 170 configures output gain control units 132L, 132R to attenuate output images to display 151. Imaging mode controller 170 then sends a command to power and level controller 115 to change the illumination source to white light source 111 with the normal illumination output level. DELAY IMAGING MODE SWITCH process 272 transfers processing to SWITCH IMAGING MODE process 273.

In SWITCH IMAGING MODE process 273, imaging mode controller 170 configures output gain control units 132L, 132R to allow display 151 to display images in the normal imaging mode. Since output images to display were greatly attenuated when the change in illumination was made, the prior art blooming is prevented. Thus, the surgeon sees a smooth transition from the fluorescence imaging mode to the normal imaging mode without any sudden bright distortion in the displayed scenes.

When the imaging mode switch command is from a high overall scene luminance to a low overall scene luminance, MODE SWITCH check operation 271 transfers to SWITCH ILLUMINATION process 274. In SWITCH ILLUMINATION process 274, imaging mode controller 170 sends a command to power and level controller 115 to turn-on fluorescence excitation source 112 and to configure white light source 111 for the fluorescence imaging mode of operation. As explained above, in one aspect, white light source 111 is turned off.

In another aspect, in process 274, the output level of white light source 111 is reduced to one part in ten relative to the normal illumination output level of white light source 111 in the normal imaging mode. In yet another aspect, one or more visible color component illumination sources are turned off and the output level of the visible color component illumination sources that remain on is reduced to one part in ten relative to the normal illumination output level of those sources in the normal imaging mode. The output level reductions are illustrative only and are not intended to be limiting to the specific values described. In this direction of change in overall scene luminance, it is unnecessary to block output to display 151 because the overall scene luminance is being decreased and so blooming is not an issue.

Figure 3:
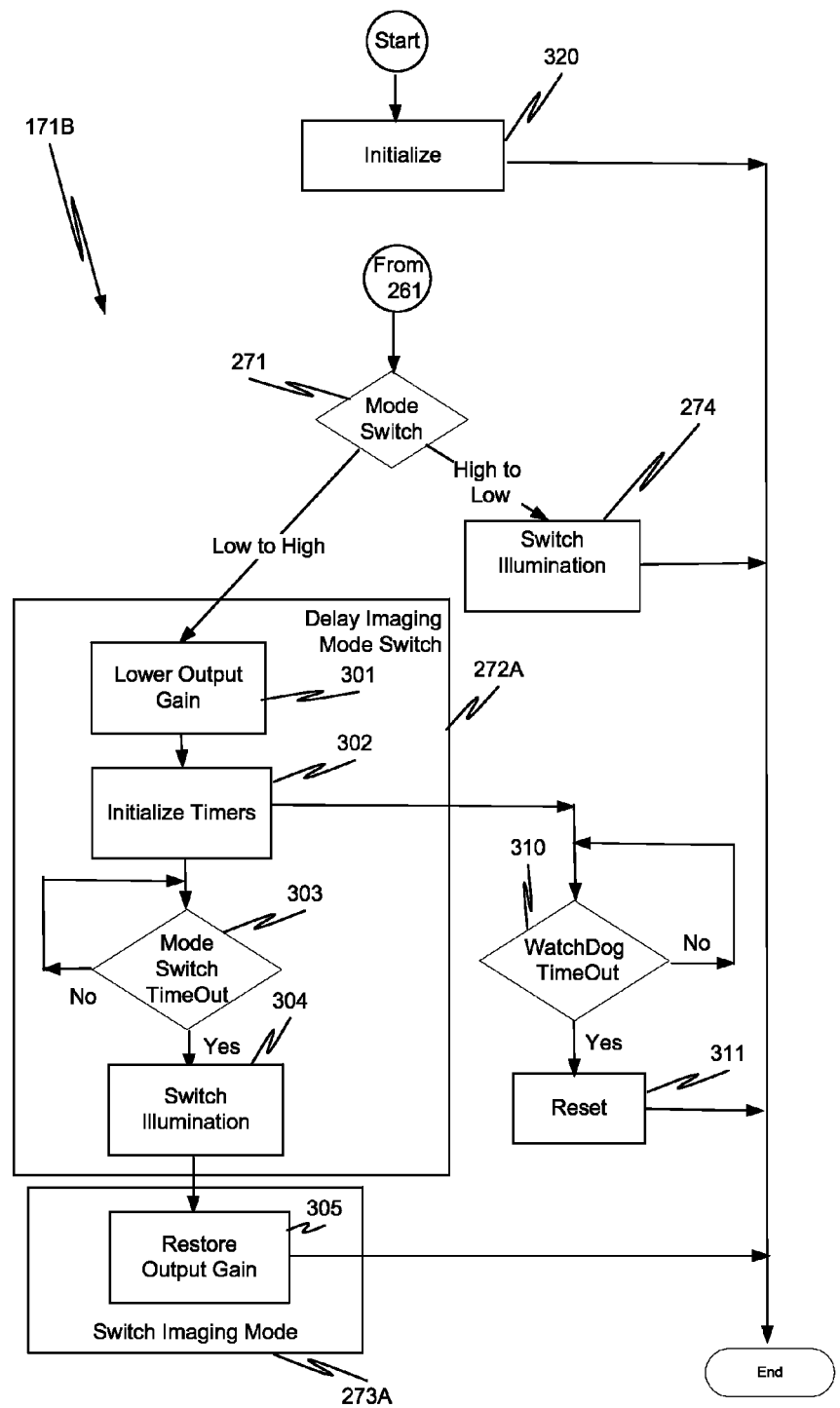
FIG. 3 is a more detailed process flow diagram for one aspect of the scene anti-bloom process.

FIG. 3 is a more detailed process flow diagram of one aspect of scene anti-bloom process 171. Initially in process 171B when system 100 is initialized, system process 162 calls INITIALIZE process 320. In this aspect, INITIALIZE process 320 communicates with each of output gain control units 132L, 132R, and instructs output gain control units 132L, 132R to send processes 272A and 273A information necessary to change the display output gains in output gain control units 132L, 132R. INITIALIZE process 320 also communicates with power and level controller 115 in dual mode illuminator 110 to initialize power and level controller 115. Upon completion, INITIALIZE process 320 ends and returns.

Processes 271 and 274 were described above and so that description is incorporated herein by reference with respect to FIG. 3. When the imaging mode switch is low to high, processing transfers from MODE SWITCH check operation 271 to DELAY IMAGING MODE SWITCH process 272A, which is an example of delay display switch process 272.

In process 272A, LOWER OUTPUT GAIN process 301 communicates with output gain control units 132L, 132R and instructs output control gain units 132L, 132R to lower the display output gain from the normal display output gain used in the normal imaging mode. The display output gain is lowered so that irrespective of the overall scene luminance of an acquired frame from cameras 120L, 120R, any images displayed on stereoscopic display 151 are greatly attenuated, i.e., display 151 goes dim.

In one aspect, as many as three different commands are issued to output gain control units 132L, 132R over a 9600 Baud communication link. Hence, there is a delay associated with lowering the display output gain. In this aspect, INITIALIZE TIMERS process 302 initializes a mode switch timer that is used to provide configurable delays between various commands that are sent. If scene anti-bloom process 171B should fail after initiation of LOWER OUTPUT GAIN process 301 and before completion of RESTORE OUTPUT GAIN process 305, display 151 would be left in the blacked out state, which is unsafe. Thus, INITIALIZE TIMERS process 302 also taps a system watchdog timer.

A system WATCHDOG TIMEOUT check operation 310 monitors the system watchdog timer. If the system watchdog timer times out, check operation 310 transfers to a RESET process 311. In RESET process 311, camera control units 130L, 130R are commanded to reload a default configuration, which is the normal imaging mode white light settings. RESET process 311 also commands power and level controller 115 to reload the default configuration, which turns off fluorescence excitation source 112, if necessary; turns on white light source 111, if necessary; and sets white light source 111 at the normal illumination output level. This process restores acquisition of useful images by cameras 120L, 120R that are displayed on display 151.

Returning to INITIALIZE TIMERS process 302, after initializing the mode switch timer, process 302 transfers to MODE SWITCH TIMEOUT check operation 303. When the mode switch timer times out, sufficient time has passed that the necessary commands have been sent to output gain control units 132L, 132R during the time period, and the display output gains of output gain control units 132L, 132R have been lowered. Thus, when the mode switch timer times out, processing transfers to SWITCH ILLUMINATION process 304.

In SWITCH ILLUMINATION process 304, a command is sent to power and level controller 115 to turn-off fluorescence excitation source 112; to turn-on white light source 111, if necessary; and to restore white light source 111 to the normal illumination output level. In one aspect, two commands are sent during process 304. This completes DELAY IMAGING MODE process 272A, and so SWITCH ILLUMINATION process 304 transfers to SWITCH IMAGING MODE process 273A, which is an example of SWITCH IMAGING MODE process 273.

RESTORE OUTPUT GAIN process 305, in SWITCH IMAGING MODE process 273A, communicates with output gain control units 132L, 132R and instructs output gain control units 132L, 132R to restore the display output gain to the normal display output gain of the normal imaging mode. When the display output gain is restored to normal, any transients in automatic gain controllers 131L, 131R have died out. Thus, when the surgeon switches the imaging mode from the fluorescence imaging mode to the normal imaging mode there is no blooming. Anti-bloom process 171B typically takes between 0.2 and 0.5 seconds to complete and so the display goes momentarily dim and then switches to the normal imaging mode. Typically, however, the surgeon does not notice the display going momentarily dim and is not distracted by this momentary display change.

The particular time aspects in processes 171, 171A, 171B depend on the camera control units used, the location of output gain control units 132L, 132R, the speed of communication links, the processing power of the hardware processor etc. Thus, the timing of when the white light source is returned to the normal illumination output level may vary. However, in each instance, the white light source is returned to the normal illumination output level after the display output gains have been lowered from the normal gain and before the display output gains are returned to the normal gain. Also, if the communications with the output gain control units are more rapid, the time required for the automatic gain controllers to settle out after the white light source has been restored to the full output level may need to be explicitly accounted for with a timeout timer or some other means.

Thus, in one aspect, a plurality of programmable time delays are used in processes 171, 171A, 171B. For example, a first programmable time delay 172 and a second programmable time delay 173 are used (FIG. 1). In one aspect, first and second programmable time delays 172, 173 are storage registers that are set to first and second values respectively during initialization of the process. The values are the delay time periods.

Storage registers are illustrative only and are not intended to be limiting. A storage register is an example of a storage element.

The delay time period of the delay in returning the white light source to the normal illumination output level is determined by first programmable time delay 172. The delay time period of the delay in switching the viewing mode after returning the white light source to the normal illumination output level is determined by second programmable time delay 173. The first and second programmable time delays 172, 173 are chosen to provide the appropriate synchronization between left and right camera control units 130L, 130R and other equipment to eliminate the blooming. Thus, either of first and second programmable time delays 172, 173 can be set to zero if the delay is not needed.

In one aspect of the fluorescence imaging mode, as discussed above, the scene on display 151 includes a simultaneous display of a reflected visible light image of tissue referred to as a backlight image, and a separately or simultaneously acquired enhanced image of tissue in the same surgical site. The enhanced image of tissue may be captured with technologies such as, but not limited to, near-infrared (NIR) fluorescence, visible light fluorescence, multispectral imaging, fluorescence lifetime imaging, or a raster scan of non-visible light characteristics that contains clinical information with spatial variation. In addition, the enhanced image may be of an image constructed by overlaying point measurements of different types of measurable tissue parameters such as tissue impedance, point detection of cancer, or certain cell types on the clinical white light image.

Generally, in this mode of display the backlight image is desaturated toward a grayscale or a black/white image that is displayed to the surgeon or clinician instead of a color reflected light image. Desaturation of any image pushes the red, green, and blue hues towards gray thereby removing color from an image. Enhanced information regarding the clinical image is captured using one or more enhanced imaging techniques and represented in the visible spectrum with one or more colors in registration with the desaturated backlight image.

When the enhanced information, typically invisible to the unaided eye, is represented in the visible spectrum it is false colored. Examples of false colors (also referred to as enhancement colors) to color the enhanced images are, but not limited to, green, blue, and purple that may be used to represent one or more types of signals in the non-visible electromagnetic spectrum detected by the enhanced imaging technology in the enhanced images.

The color version of the enhanced image is registered to the desaturated backlight clinical image and blended with, superimposed on, or overlaid on top of (alternatively referred to as being combined with) the desaturated clinical image. The combination of these two images in a blended image is displayed to the surgeon to increase the amount of clinically relevant information, and to improve the detectability of low signal levels in the color enhanced images of the surgical site during surgery.

As the backlight clinical image is desaturated, the color information in the image is removed but there is little loss in detail. The desaturated clinical image is sufficient to identify anatomy, tissue landmarks, and surgical instruments so that it allows safe manipulation thereof. Moreover with a desaturated clinical image, there is no loss in contrast of the enhanced image due to interference by a color representation of a white light clinical image. The color enhanced image overlaid onto the desaturated clinical image provides improved information content regarding the surgical site to reduce the risk of injury to the patient and improve surgical efficiency. More detail about this mode of display is presented in U.S. patent application Ser. No. 12/575,093 (filed Oct. 7, 2009; disclosing Methods and Apparatus for Displaying Enhanced Imaging Data on a Clinical Image), which is incorporated herein by reference in its entirety.

In the above methods, various modules and operations and/or processes were described. Each of these operations or processes is part of a module in central controller 190. While central controller 190 is illustrated as a single structure in FIG. 1, this is for ease of illustration only. The elements of central controller 190 are typically distributed throughout system 100 at appropriate locations.

Figure 4:
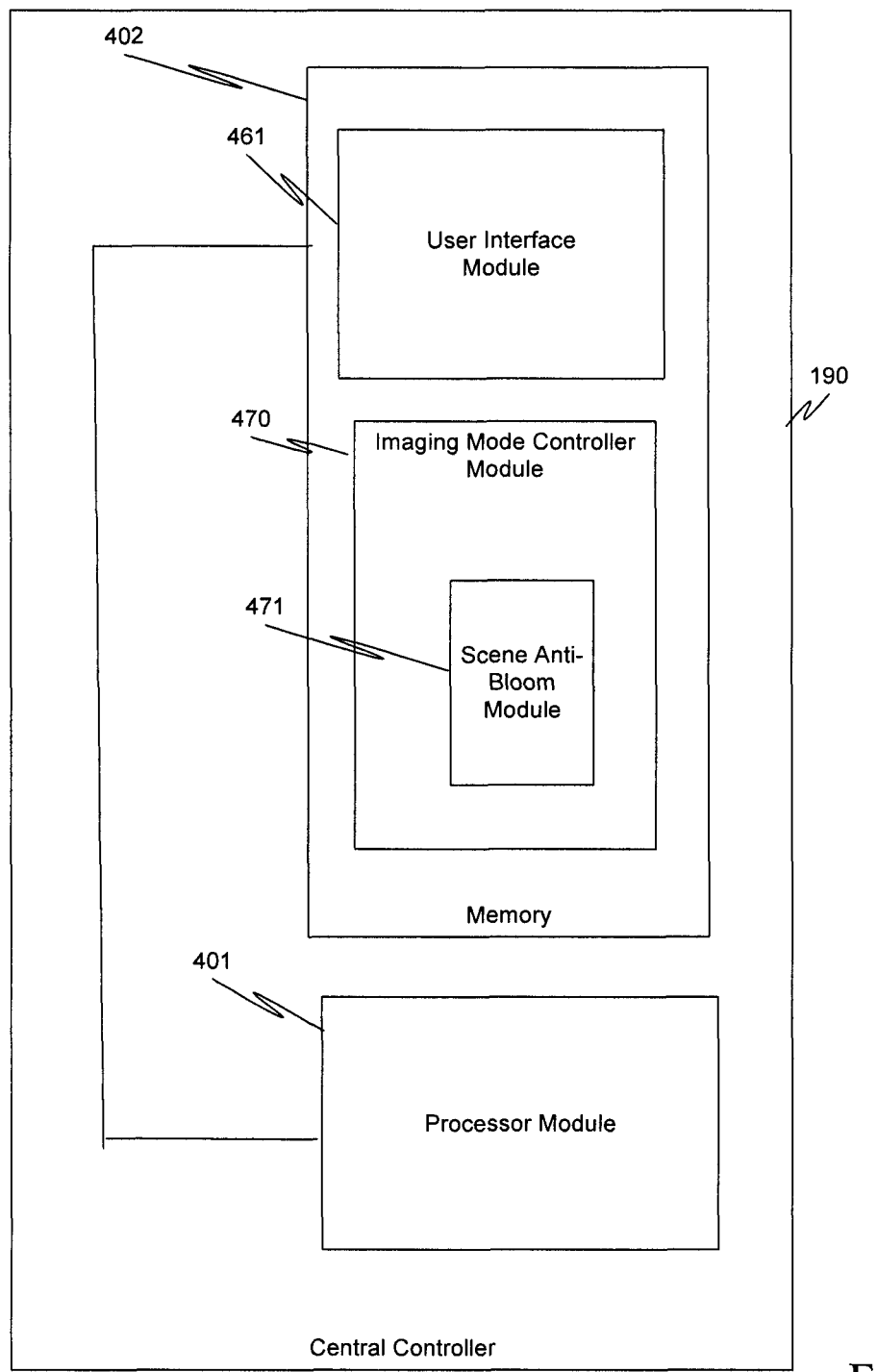
FIG. 4 is a high level diagram of modules of the minimally invasive surgical system.

User interface module 461 (FIG. 4) is used to implement user interface 161. Imaging mode controller module 470 is used to implement imaging mode controller 170. Similarly, scene anti-bloom module 471 is used to implement scene anti-bloom process 171. The modules may be implemented in hardware, software that is executed on a processor, firmware or any combination of hardware, software, or firmware. In one aspect, scene anti-bloom module includes computer executable instructions stored in memory 402. In this aspect, no hardware changes are required to implement scene anti-bloom process 171.

When the modules include one or more instructions stored on a non-transitory storage medium, the described operations and/or processes are the result of retrieval and execution of the one or more instructions on at least one processor in processor module 401. Herein, a processor is a hardware element. The particular modules described are illustrative only and are not intended to be limiting. In view of the disclosure, one knowledgeable in the field can combine modules together or separate a module into one or more additional modules.

The above description and the accompanying drawings that illustrate aspects and embodiments of the present inventions should not be taken as limiting—the claims define the protected inventions. Various mechanical, compositional, structural, electrical, and operational changes may be made without departing from the spirit and scope of this description and the claims. In some instances, well-known circuits, structures, and techniques have not been shown or described in detail to avoid obscuring the invention.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of the device in use or operation in addition to the position and orientation shown in the figures. For example, if the device in the figures is turned over, elements described as "below" or "beneath" other elements or features would then be "above" or "over" the other elements or features. Thus, the exemplary term "below" can encompass both positions and orientations of above and below. The device may be otherwise oriented (rotated 90 degrees or at other orientations) and the spatially relative descriptors used herein interpreted accordingly. Likewise, descriptions of movement along and around various axes include various special device positions and orientations.

The singular forms "a", "an", and "the" are intended to include the plural forms as well, unless the context indicates otherwise. The terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

Memory refers to a volatile memory, a non-volatile memory, or any combination of the two. A processor is coupled to a memory containing instructions executed by the processor. This could be accomplished within a computer system, or alternatively via a connection to another computer via modems and analog lines, or digital interfaces and a digital carrier line.

Herein, a computer program product includes a non-transitory medium configured to store computer readable code needed for any one or any combination of the operations described with respect to processes 171, 171A or 171B in which computer readable code for any one or any combination of operations described with respect to processes 171, 171A or 171B is stored. Some examples of computer program products are CD-ROM discs, DVD discs, flash memory, ROM cards, floppy discs, magnetic tapes, computer hard drives, servers on a network and signals transmitted over a network representing computer readable program code. A tangible non-transitory computer program product includes a tangible non-transitory medium configured to store computer readable instructions for any one of, or any combination of operations described with respect to processes 171, 171A or 171B or in which computer readable instructions for any one of, or any combination of operations described with respect to the scene anti-bloom process 171, 171A or 171B are stored. Tangible non-transitory computer program products include CD-ROM discs, DVD discs, flash memory, ROM cards, floppy discs, magnetic tapes, computer hard drives and other physical non-transitory storage mediums.

In view of this disclosure, instructions used in any one of, or any combination of operations described with respect to the processes 171, 171A or 171B can be implemented in a wide variety of computer system configurations using an operating system and computer programming language of interest to the user.

All examples and illustrative references are non-limiting and should not be used to limit the claims to specific implementations and embodiments described herein and their equivalents. The headings are solely for formatting and should not be used to limit the subject matter in any way, because text under one heading may cross reference or apply to text under one or more headings. Finally, in view of this disclosure, particular features described in relation to one aspect or embodiment may be applied to other disclosed aspects or embodiments of the invention, even though not specifically shown in the drawings or described in the text.

We claim:

1. A method comprising:
    receiving, by a controller in a surgical system, a command to switch from a first imaging mode during a surgical procedure to a second imaging mode during the surgical procedure,
    wherein the first and second imaging modes have different non-zero illumination levels,
    wherein the first imaging mode has a reduced visible illumination output level of a visible illumination source relative to a normal visible illumination output level of the visible illumination source in the second imaging mode,
    wherein in the first and second imaging modes, scenes are acquired for display,
    wherein the first and second imaging modes each have a normal level of a display output gain of a display of the surgical system, and
    wherein an overall scene luminance of an acquired scene in the first imaging mode is less than an overall scene luminance of an acquired scene in the second imaging mode;
    delaying, by the controller, the switch to the second imaging mode until after a visible illumination output level of the visible illumination source has changed from a lower visible illumination output level to a higher visible illumination output level,
    wherein the delaying further comprises lowering the display output gain of an output gain control unit from the normal level of the first imaging mode, wherein the output gain control unit is coupled between an automatic gain controller and the display; and
    switching, by the controller, to the second imaging mode after the output level of the visible illumination source has changed from the lower visible illumination output level to the higher visible illumination output level.

2. The method of claim 1, wherein the delaying further comprises:
    switching from the lower visible illumination output level of the visible illumination source to the higher visible illumination output level of the visible illumination source following the lowering the display output gain.

3. The method of claim 1, wherein the switching to the second imaging mode comprises:
    restoring the display output gain to the normal level of the second imaging mode.

4. The method of claim 1, wherein the first imaging mode includes displaying a fluorescence image on the display, and wherein the second imaging mode includes displaying a reflected visible light image on the display.

5. The method of claim 1, wherein the delaying further comprises delaying for a programmable delay time period.

6. The method of claim 1, wherein said switching further comprises:
    delaying the switching for a delay time period after the visible illumination output level of the visible illumination source has changed and then performing the switching.

7. The method of claim 6, wherein the delaying the switching comprises delaying the switching for a programmable delay time period.

8. A surgical system comprising:
    a display;
    a camera control unit including an automatic gain controller;
    an output gain control unit coupled between the automatic gain controller and the display;
    an imaging mode switch, the imaging mode switch being configured to select one of a plurality of imaging modes, the plurality of imaging modes including a first imaging mode during a surgical procedure and a second imaging mode during the surgical procedure,
        wherein in the first and second imaging modes, scenes are acquired for display, and
        wherein an overall scene luminance of an acquired scene in the first imaging mode is less than an overall scene luminance of an acquired scene in the second imaging mode;
    an illuminator comprising a power and level controller and a visible light illumination source, the visible light illumination source being coupled to the power and level controller; and
    a controller coupled to the output gain control unit, to the power and level controller, and to the imaging mode switch, following receipt of an imaging mode change command from the imaging mode switch, the imaging mode change command being a command to change from the first imaging mode during the surgical procedure to the second imaging mode during the surgical procedure, the first and second imaging modes having different non-zero illumination levels, the first imaging mode having a reduced visible illumination output level relative to a normal visible illumination output level of the second imaging mode, the controller being configured to delay the image mode change until after an illumination output level change of the visible light illumination source from the reduced visible illumination output level to the normal visible illumination output level, the controller being configured to configure the output gain control unit to attenuate any image output to the display during the delay, the controller being configured to configure the power and level controller to restore an illumination output level of the visible light illumination source from the reduced visible illumination output level to the normal visible illumination output level during the delay, and the controller being configured to switch to the second imaging mode after the normal visible illumination output level of the visible light illumination source has been restored.

9. The system of claim 8, wherein the reduced visible illumination output level corresponds to the visible light illumination source being powered off.

10. The system of claim 8, wherein the reduced visible illumination output level is less than one hundred percent of the normal visible illumination output level.

11. The system of claim 8, further comprising:
a programmable time delay storage element comprising a delay time period before the controller configures the power and level controller to restore the normal visible illumination output level.

12. The system of claim 8, wherein following the restoration of the normal visible illumination output level of the visible light illumination source, the controller configures the camera control unit to display an image on the display.

13. The system of claim 12, further comprising:
a programmable time delay storage element comprising a delay time period after the restoration of the normal visible illumination output level of the visible light illumination source by the controller and before the controller configures the camera control unit to display an image on the display.

14. The system of claim 8, wherein the output gain control unit is included in the camera control unit.

15. A method comprising:
lowering an output gain of a display from the normal level of a first imaging mode following receipt of an imaging mode switch command by a controller in a surgical system, the lowering being by the controller, the imaging mode switch command being a command to switch from the first imaging mode to a second imaging mode,
wherein the first and second imaging modes have different non-zero illumination levels,
wherein the first imaging mode has a reduced visible illumination output level of an illumination unit relative to a normal visible illumination output level of the illumination unit in the second imaging mode,
wherein in the first and second imaging modes, scenes are acquired for display, and
wherein an overall scene luminance of an acquired scene in the first imaging mode is less than an overall scene luminance of an acquired scene in the second imaging mode;
commanding the illumination unit to switch from a first visible illumination level to a second visible illumination level following a first predetermined time period after the lowering, the commanding being by the controller, wherein the second visible illumination level is larger than the first visible illumination level; and
restoring the output gain of the display, the restoring being by the controller, wherein the output gain of the display is different from an automatic gain controlled by an automatic gain controller.

16. The method of claim 15, further comprising delaying the restoring a second predetermined time period following the illumination unit switching to the second visible illumination level.

\* \* \* \* \*